(12) United States Patent
Tammer et al.

(10) Patent No.: US 12,209,065 B2
(45) Date of Patent: *Jan. 28, 2025

(54) PROCESS FOR THE PRODUCTION OF DIACYL PEROXIDES

(71) Applicant: NOURYON CHEMICALS INTERNATIONAL B.V., Arnhem (NL)

(72) Inventors: Martinus Catharinus Tammer, Diepenveen (NL); Auke Gerardus Talma, Bathmen (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 636 days.

This patent is subject to a terminal disclaimer.

(21) Appl. No.: 17/596,381

(22) PCT Filed: Jun. 11, 2020

(86) PCT No.: PCT/EP2020/066229
§ 371 (c)(1),
(2) Date: Dec. 9, 2021

(87) PCT Pub. No.: WO2020/249690
PCT Pub. Date: Dec. 17, 2020

(65) Prior Publication Data
US 2022/0235002 A1 Jul. 28, 2022

(30) Foreign Application Priority Data
Jun. 12, 2019 (EP) .................................. 19179622

(51) Int. Cl.
*C07C 407/00* (2006.01)
*C07C 51/083* (2006.01)
*C07C 51/41* (2006.01)
*C07C 51/56* (2006.01)

(52) U.S. Cl.
CPC .......... *C07C 407/00* (2013.01); *C07C 51/083* (2013.01); *C07C 51/412* (2013.01); *C07C 51/56* (2013.01); *C07C 407/003* (2013.01)

(58) Field of Classification Search
CPC ... C07C 407/00; C07C 409/34; C07C 409/36; C07C 407/003; C07C 51/083; C07C 53/00; C07C 51/412; C07C 51/56
See application file for complete search history.

(56) References Cited

U.S. PATENT DOCUMENTS

| | | | |
|---|---|---|---|
| 968,804 A | 8/1910 | Rigby | |
| 2,589,112 A | 3/1952 | Moise et al. | |
| 3,079,443 A | 2/1963 | Barrett et al. | |
| 3,138,627 A | 6/1964 | Harrison et al. | |
| 3,264,346 A | 8/1966 | Weiberg | |
| 3,397,245 A | 8/1968 | Appel et al. | |
| 3,502,701 A | 3/1970 | Lewis et al. | |
| 3,580,955 A | 5/1971 | Bafford | |
| 3,595,898 A | 7/1971 | Harvey et al. | |
| 3,956,396 A | 5/1976 | Mageli et al. | |
| 4,002,539 A | 1/1977 | Strohmeyer et al. | |
| 4,087,623 A | 5/1978 | Sherwin et al. | |
| 4,613,463 A | 9/1986 | Sacks | |
| 5,021,607 A | 6/1991 | Huybrechts | |
| 5,281,571 A | 1/1994 | Woodard et al. | |
| 5,654,463 A | 8/1997 | Abma et al. | |
| 6,040,331 A | 3/2000 | Yamamoto et al. | |
| 6,331,597 B1 | 12/2001 | Drumright et al. | |
| 6,592,990 B2 | 7/2003 | Schwantes | |
| 6,610,880 B1 | 8/2003 | Overkamp et al. | |
| 6,803,420 B2 | 10/2004 | Cleary et al. | |
| 7,049,467 B2 | 5/2006 | Paul et al. | |
| 7,084,088 B2 | 8/2006 | Nishikido et al. | |
| 7,112,314 B2 | 9/2006 | Brothers et al. | |
| 7,253,312 B2 | 8/2007 | Bonnet et al. | |
| 7,476,260 B2 | 1/2009 | Eliu et al. | |
| 7,511,068 B2 | 3/2009 | Van Lommen et al. | |
| 7,544,694 B2 | 6/2009 | Janssens et al. | |
| 7,612,056 B2 | 11/2009 | Janssens et al. | |
| 7,700,707 B2 | 4/2010 | Abhari et al. | |
| 7,714,038 B2 | 5/2010 | Haering et al. | |
| 7,799,093 B2 | 9/2010 | Brun et al. | |
| 7,875,678 B2 | 1/2011 | Hanner et al. | |
| 7,915,249 B2 | 3/2011 | Cid-Nunez et al. | |
| 8,017,801 B2 | 9/2011 | Appel et al. | |
| 8,148,388 B2 | 4/2012 | Freyne et al. | |
| 8,152,781 B2 | 4/2012 | Yang | |
| 8,337,822 B2 | 12/2012 | Brun | |
| 8,586,791 B2 | 11/2013 | Ansai et al. | |
| 8,609,883 B2 | 12/2013 | Appel et al. | |
| 8,663,459 B2 | 3/2014 | Al-Shahrani et al. | |
| 8,680,299 B2 | 3/2014 | Scutt | |
| 8,735,413 B2 | 5/2014 | Connolly et al. | |
| 8,741,127 B2 | 6/2014 | Koseoglu et al. | |
| 8,741,274 B2 | 6/2014 | Van et al. | |
| 8,853,426 B2 | 10/2014 | Ishihara et al. | |
| 9,017,648 B2 | 4/2015 | Barba et al. | |
| 9,018,417 B2 | 4/2015 | Frey et al. | |
| 9,090,548 B2 | 7/2015 | Cerd et al. | |
| 9,119,879 B2 | 9/2015 | Du-Thumm et al. | |
| 9,127,026 B2 | 9/2015 | Mariot et al. | |
| 9,212,136 B2 | 12/2015 | Bader et al. | |
| 9,221,028 B2 | 12/2015 | Dihora et al. | |
| 9,388,175 B2 | 7/2016 | Thuring et al. | |
| 9,416,109 B2 | 8/2016 | Moniz et al. | |
| 9,422,217 B2 | 8/2016 | Kon et al. | |
| 9,649,264 B2 | 5/2017 | Ferrari et al. | |

(Continued)

FOREIGN PATENT DOCUMENTS

| AU | 5310473 A | 9/1974 |
|---|---|---|
| CA | 488970 A | 12/1952 |

(Continued)

*Primary Examiner* — Amy C Bonaparte
(74) *Attorney, Agent, or Firm* — LORENZ & KOPF, LLP

(57) ABSTRACT

Process for the production of a diacyl peroxide involving the reaction of an anhydride with a peroxyacid, removal of the formed carboxylic acid, production of an anhydride from said carboxylic acid, and recycling of the anhydride within the process.

17 Claims, No Drawings

(56) References Cited

U.S. PATENT DOCUMENTS

| | | | |
|---|---|---|---|
| 10,011,552 | B2 | 7/2018 | Bristow |
| 10,206,947 | B2 | 2/2019 | Doxey et al. |
| 10,226,483 | B2 | 3/2019 | Doxey et al. |
| 10,272,164 | B2 | 4/2019 | Campbell et al. |
| 10,573,443 | B2 | 2/2020 | Seidel et al. |
| 10,870,817 | B2 | 12/2020 | Findlay et al. |
| 11,066,502 | B2 | 7/2021 | Ulmer et al. |
| 11,266,584 | B2 | 3/2022 | Tachon et al. |
| 2003/0004369 | A1 | 1/2003 | Krasutsky et al. |
| 2005/0014974 | A1 | 1/2005 | Paul et al. |
| 2005/0015974 | A1 | 1/2005 | Frutschy et al. |
| 2005/0070664 | A1 | 3/2005 | Takashima et al. |
| 2005/0119501 | A1 | 6/2005 | Tammer et al. |
| 2005/0165600 | A1 | 7/2005 | Kasravi et al. |
| 2007/0213346 | A1 | 9/2007 | Janssens et al. |
| 2007/0224158 | A1 | 9/2007 | Cassin et al. |
| 2008/0226581 | A1 | 9/2008 | Luukas |
| 2009/0280069 | A1 | 11/2009 | Godowski |
| 2010/0003205 | A1 | 1/2010 | Elliott et al. |
| 2010/0003293 | A1 | 1/2010 | Elliott et al. |
| 2010/0074928 | A1 | 3/2010 | Elliott et al. |
| 2010/0031048 | A1 | 12/2010 | Claudia |
| 2011/0136704 | A1 | 6/2011 | Sharma et al. |
| 2011/0268778 | A1 | 11/2011 | Dihora et al. |
| 2011/0269657 | A1 | 11/2011 | Dihora et al. |
| 2012/0196988 | A1 | 8/2012 | Gaboardi et al. |
| 2013/0142743 | A1 | 6/2013 | Cavazzuti et al. |
| 2015/0099845 | A1 | 4/2015 | Daga et al. |
| 2016/0213600 | A1 | 7/2016 | Klostermann et al. |

FOREIGN PATENT DOCUMENTS

| | | | |
|---|---|---|---|
| CA | 1120055 | A | 3/1982 |
| CA | 2167279 | A1 | 2/1995 |
| CN | 1061777 | A | 6/1992 |
| CN | 1151421 | A | 6/1997 |
| CN | 1172105 | A | 2/1998 |
| CN | 1342647 | A | 4/2002 |
| CN | 1343247 | A | 4/2002 |
| CN | 1368981 | A | 9/2002 |
| CN | 1100771 | C | 2/2003 |
| CN | 1427771 | A | 7/2003 |
| CN | 1463282 | A | 12/2003 |
| CN | 1519649 | A | 8/2004 |
| CN | 1537131 | A | 10/2004 |
| CN | 1575204 | A | 2/2005 |
| CN | 1660498 | A | 8/2005 |
| CN | 1714068 | A | 12/2005 |
| CN | 1720266 | A | 1/2006 |
| CN | 1745069 | A | 3/2006 |
| CN | 1847289 | A | 10/2006 |
| CN | 1860197 | A | 11/2006 |
| CN | 1933808 | A | 3/2007 |
| CN | 1938291 | A | 3/2007 |
| CN | 1942471 | A | 4/2007 |
| CN | 1946723 | A | 4/2007 |
| CN | 101107254 | A | 1/2008 |
| CN | 101133091 | A | 2/2008 |
| CN | 101249046 | A | 8/2008 |
| CN | 101249047 | A | 8/2008 |
| CN | 101263130 | A | 9/2008 |
| CN | 100421646 | C | 10/2008 |
| CN | 100540079 | C | 9/2009 |
| CN | 101522177 | A | 9/2009 |
| CN | 101522570 | A | 9/2009 |
| CN | 1986635 | B | 5/2010 |
| CN | 1911971 | B | 11/2010 |
| CN | 101072779 | B | 12/2010 |
| CN | 102076317 | A | 5/2011 |
| CN | 102076318 | A | 5/2011 |
| CN | 102076319 | A | 5/2011 |
| CN | 102088956 | A | 6/2011 |
| CN | 102092902 | A | 6/2011 |
| CN | 102092904 | A | 6/2011 |
| CN | 102092906 | A | 6/2011 |
| CN | 102093909 | A | 6/2011 |
| CN | 102131773 | A | 7/2011 |
| CN | 102574933 | A | 7/2012 |
| CN | 102666614 | A | 9/2012 |
| CN | 102844054 | A | 12/2012 |
| CN | 102858940 | A | 1/2013 |
| CN | 1997340 | B | 7/2013 |
| CN | 103228272 | A | 7/2013 |
| CN | 103622842 | A | 3/2014 |
| CN | 104093691 | A | 10/2014 |
| CN | 104394835 | A | 3/2015 |
| CN | 104672079 | A | 6/2015 |
| CN | 103649278 | B | 6/2016 |
| CN | 105705481 | A | 6/2016 |
| CN | 105765672 | A | 7/2016 |
| CN | 105793344 | A | 7/2016 |
| CN | 105813617 | A | 7/2016 |
| CN | 102858944 | B | 8/2016 |
| CN | 104114524 | B | 8/2016 |
| CN | 104114627 | B | 9/2016 |
| CN | 105979969 | A | 9/2016 |
| CN | 106029052 | A | 10/2016 |
| CN | 106278875 | A | 1/2017 |
| CN | 102627778 | B | 4/2017 |
| CN | 108423908 | A | 8/2018 |
| CN | 109331871 | A | 2/2019 |
| DE | 1518741 | C2 | 6/1980 |
| EP | 0323663 | A2 | 7/1989 |
| EP | 0616505 | B1 | 9/1996 |
| EP | 0682695 | B1 | 10/1997 |
| EP | 0639577 | B1 | 5/2002 |
| EP | 1220837 | B1 | 8/2004 |
| EP | 1445120 | B1 | 7/2007 |
| EP | 1383824 | B1 | 10/2008 |
| EP | 1372580 | B1 | 9/2010 |
| EP | 2666763 | A1 | 11/2013 |
| EP | 3047845 | B1 | 6/2017 |
| FR | 2366059 | A1 | 4/1978 |
| GB | 444603 | A | 3/1936 |
| GB | 901041 | A | 7/1962 |
| GB | 1135372 | A | 12/1968 |
| GB | 1156573 | A | 7/1969 |
| JP | H01249752 | A | 10/1989 |
| JP | H08245605 | A | 9/1996 |
| JP | H08281077 | A | 10/1996 |
| JP | 2003511440 | A | 3/2003 |
| JP | 2004315536 | A | 11/2004 |
| JP | 2006016393 | A | 1/2006 |
| JP | 2007099624 | A | 4/2007 |
| JP | 3921507 | B2 | 5/2007 |
| JP | 4009007 | B2 | 11/2007 |
| JP | 4317185 | B2 | 8/2009 |
| JP | 2009542756 | A | 12/2009 |
| JP | 2009542757 | A | 12/2009 |
| JP | 2014064971 | A | 4/2014 |
| JP | 2015523968 | A | 8/2015 |
| KR | 1020140037915 | A | 3/2014 |
| KR | 1020140099550 | A | 8/2014 |
| KR | 1020150023843 | A | 3/2015 |
| RU | 2286801 | C2 | 11/2006 |
| RU | 2656332 | C1 | 6/2018 |
| WO | 0046332 | A1 | 8/2000 |
| WO | 02098924 | A2 | 12/2002 |
| WO | 2010016493 | A1 | 2/2010 |
| WO | 2020157061 | A1 | 8/2020 |

PROCESS FOR THE PRODUCTION OF DIACYL PEROXIDES

CROSS-REFERENCE TO RELATED APPLICATION

This application is a U.S. National-Stage entry under 35 U.S.C. § 371 based on International Application No. PCT/EP2020/066229, filed Jun. 11, 2020 which was published under PCT Article 21(2) and which claims priority to European Application No. 19179622.6, filed Jun. 12, 2019, which are all hereby incorporated in their entirety by reference.

TECHNICAL FIELD

This disclosure relates to a process for the preparation of diacyl peroxides.

BACKGROUND

Diacyl peroxides have the general formula

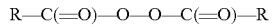

wherein the R-groups may be the same or different and are selected from aryl, arylalkyl, and linear, branched, or cyclic alkyl groups, optionally substituted with heteroatom-containing substituents.

Symmetrical diacyl peroxides, that is, those in which the R-groups in the above formula are the same, have been prepared by reacting an excess of acid anhydride or acid chloride with alkaline solutions of hydrogen peroxide, as illustrated by the following equations:

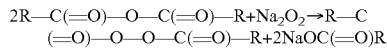

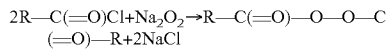

In this reaction scheme, $Na_2O_2$ does not refer to the discrete product $Na_2O_2$, but to an equilibrium comprising $H_2O_2$ and NaOOH.

U.S. Pat. No. 3,580,955 discloses a process for the preparation of asymmetrical diacyl peroxides by reacting an acid chloride with an aldehyde and oxygen in the presence of an acid receptor.

U.S. Pat. No. 3,502,701 produces asymmetrical diacyl peroxides by reacting an acid chloride with peroxyacid.

Acid chlorides are relatively expensive and generate chloride-containing water layers, which lead to waste waters with high salt concentration.

Another process that allows for the preparation of asymmetrical diacyl peroxides has been described in GB 1,156,573, and involves the reaction between an organic anhydride, an aldehyde, and oxygen, in the presence of a catalyst that comprises the lithium or magnesium salt of an organic acid.

GB 444,603 discloses the preparation of acetyl benzoyl peroxide by reacting benzaldehyde and acetic anhydride with an oxygen-containing gas in the presence of dibenzoyl peroxide.

Anhydrides, however, are even more expensive than acid chlorides and the waste stream of this process contains a high organic load—i.e. a high Chemical Oxygen Demand (COD) value—due to the formed carboxylic acid salt, and is therefore economically and environmentally unattractive.

GB 901,041 discloses a process of preparing diacyl peroxides by reacting a peracid with an anhydride or a halide of an organic acid, wherein using the chloride is said to be preferred.

It is an object of the present disclosure to provide a process for the production of diacyl peroxides that has a relatively low carboxylic acid (salt) content in its effluent and does not require the use of acid chlorides.

BRIEF SUMMARY

This disclosure provides a process for the production of a diacyl peroxide comprising the following steps:
a) producing a mixture comprising a diacyl peroxide and a carboxylic acid by reacting an anhydride with the formula $R^1$—C(=O)—O—C(=O)—$R^2$ with a peroxyacid of the formula $R^3$—C(=O)—OOH,
wherein $R^1$ and $R^3$ are independently selected from linear and branched alkyl, cycloalkyl, aryl, and arylalkyl groups with 1 to about 17 carbon atoms, optionally substituted with oxygen- and/or halogen-containing substituents, and $R^2$ is selected from linear and branched alkyl, cycloalkyl, aryl, and arylalkyl groups with about 2 to about 17 carbon atoms, optionally substituted with oxygen- and/or halogen-containing substituents,
b) extracting or separating the carboxylic acid from the mixture in the form of its carboxylic acid salt or adduct,
c) liberating the carboxylic acid from the salt or adduct,
d) optionally producing an additional amount of carboxylic acid by reacting an aldehyde of the formula $R^2$—C(=O)H with oxygen,
e) reacting the carboxylic acid obtained in step c) and optionally an additional amount of carboxylic acid of the formula $R^2$—C(=O)OH—said additional amount of carboxylic acid being obtained from step d) and/or obtained in another way—with an acid anhydride or a ketene of the formula $C(R^4)_2$=C=O, each $R^4$ being independently selected from H and $CH_3$ to form an anhydride with the formula $R^1$—C(=O)—O—C(=O)—$R^2$, and
f) recycling at least part of the anhydride formed in step e) to step a).

DETAILED DESCRIPTION

The following detailed description is merely exemplary in nature and is not intended to limit the disclosure or the application and uses of the disclosure. Furthermore, there is no intention to be bound by any theory presented in the preceding background of the disclosure or the following detailed description.

This object of this disclosure can be achieved by a process comprising the following steps:
a) producing a mixture comprising a diacyl peroxide and a carboxylic acid by reacting an anhydride with the formula $R^1$—C(=O)—O—C(=O)—$R^2$ with a peroxyacid of the formula $R^3$—C(=O)—OOH,
wherein $R^1$ and $R^3$ are independently selected from linear and branched alkyl, cycloalkyl, aryl, and arylalkyl groups with 1 to about 17 carbon atoms, optionally substituted with oxygen- and/or halogen-containing substituents, and R2 is selected from linear and branched alkyl, cycloalkyl, aryl, and arylalkyl groups with about 2 to about 17 carbon atoms, optionally substituted with oxygen- and/or halogen-containing substituents,
b) extracting or separating the carboxylic acid from the mixture in the form of its carboxylic acid salt or adduct, c) liberating the carboxylic acid from the salt or adduct,
d) optionally producing an additional amount of carboxylic acid by reacting an aldehyde of the formula $R^2$—C(=O)H with oxygen,
e) reacting the carboxylic acid obtained in step c) and optionally an additional amount of carboxylic acid of the formula $R^2$—C(=O)OH—said additional amount of carboxylic acid being obtained from step d) and/or obtained in another way—with an acid anhydride or a ketene of the formula $C(R^4)_2$=C=O, each $R^4$ being independently selected from H and $CH_3$, preferably with acetic anhydride, to form an anhydride with the formula $R^1$—C(=O)—O—C(=O)—$R^2$, and
f) recycling at least part of the anhydride formed in step e) to step a).

This process produces a diacyl peroxide from an anhydride, which anhydride is obtained at least partly from the carboxylic acid side product. This re-use of the carboxylic acid formed in step a) makes the route economically attractive and its effluents low in COD.

Preferably, any additional amount of carboxylic acid that is required to form the amount of anhydride that is needed in step a) is obtained by oxidation of the corresponding aldehyde. It is therefore preferred to produce an additional amount of carboxylic acid in step d) and react it in step e) with acetic anhydride or a ketene.

As this process does not involve the use of corrosive or volatile reactants, it increases production safety and allows production at the location in which the diacyl peroxide is eventually used (e.g. a polymerization facility). Such on-site production allows peroxide production on demand, thereby minimizing storage capacities and the consequential safety measures.

Step a) involves the reaction of a peroxyacid with an anhydride with the formula $R^1$—C(=O)—O—C(=O)—$R^2$.

R1 in this formula is selected from linear and branched alkyl, cycloalkyl, aryl, and arylalkyl groups with 1 to about 17 carbon atoms, optionally substituted with oxygen- and/or halogen-containing substituents. Examples of suitable substituents are alkoxy, chlorine, and ester substituents. The number of carbon atoms is preferably about 2 to about 11, even more preferably 2-8, and most preferably about 3 to about 6 carbon atoms. In a further preferred embodiment, R1 is selected from linear or branched alkyl groups. Most preferably, $R^1$ is selected from the group of n-propyl, n-butyl, 2-butyl and isopropyl groups.

$R^2$ in this formula is selected from linear and branched alkyl, cycloalkyl, aryl, and arylalkyl groups with about 2 to about 17 carbon atoms, optionally substituted with oxygen- and/or halogen-containing substituents. Examples of suitable substituents are alkoxy, chlorine, and ester substituents. The number of carbon atoms is preferably about 2 to about 11, even more preferably about 2 to about 8, and most preferably about 3 to about 6 carbon atoms. In a further preferred embodiment, $R^2$ is selected from linear or branched alkyl groups. Most preferably, $R^2$ is selected from the group of n-propyl, n-butyl, 2-butyl and isopropyl groups.

The anhydride can be symmetrical, meaning $R^1$=$R^2$, or asymmetrical, meaning that the $R^1 \neq R^2$.

If the anhydride is symmetrical, the carboxylic acid that is formed in step a) and extracted or separated in step b) will have the formula $R^2$—C(=O)OH. If the anhydride is asymmetrical, the carboxylic acid will be a mixture of $R^2$—C(=O)OH and $R^1$—C(=O)OH.

Suitable symmetrical anhydrides are propionic anhydride, n-butyric anhydride, isobutyric anhydride, pivalic anhydride, valeric anhydride, isovaleric anhydride, 2-methyl butyric anhydride, 2-methylpentanoic anhydride, 2-methylhexanoic anhydride, 2-methylheptanoic anhydride, 2-ethyl butyric anhydride, caproic anhydride, caprylic anhydride, isocaproic anhydride, n-heptanoic anhydride, nonanoic anhydride, isononanoic anhydride, 3,5,5-trimethylhexanoic anhydride, 2-propylheptanoic anhydride, decanoic anhydride, neodecanoic anhydride, undecanoic anhydride, neoheptanoic anhydride, lauric anhydride, tridecanoic anhydride, 2-ethyl hexanoic anhydride, myristic anhydride, palmitic anhydride, stearic anhydride, phenylacetic anhydride, cyclohexanecarboxylic anhydride, 3-methyl-cyclopentanecarboxylic anhydride, beta-methoxy propionic anhydride, methoxy acetic anhydride, ethoxy acetic anhydride, propoxy acetic anhydride, alpha-ethoxy butyric anhydride, benzoic anhydride, o-, m-, and p-toluic anhydride, 2,4,6-trimethylbenzoic anhydride, o-, m-, and p-chlorobenzoic anhydride, o-, m-, and p-bromobenzoic anhydride, o-, m-, and p-nitrobenzoic anhydride, o-, m-, and p-methoxybenzoic anhydride, and mixtures of two or more of the above-mentioned anhydrides.

Examples of suitable mixtures of symmetrical anhydrides are the mixture of isobutyric anhydride and 2-methylbutyric anhydride, the mixture of isobutyric anhydride and 2-methylpentanoic anhydride, the mixture of 2-methylbutyric anhydride and isovaleric anhydride, and the mixture of 2-methylbutyric anhydride and valeric anhydride.

Asymmetrical anhydrides are usually available as a mixture of the asymmetrical and symmetrical anhydrides. This is because asymmetrical anhydrides are usually obtained by reacting a mixture of acids with, e.g., acetic anhydride. This leads to a mixture of anhydrides, including an asymmetrical and at least one symmetrical anhydride. Such mixtures of anhydrides can be used in the process of the present disclosure. Examples of suitable asymmetrical anhydrides are isobutyric-2-methylbutyric anhydride, which is preferably present as admixture with isobutyric anhydride and 2-methylbutyric anhydride; isobutyric-acetic anhydride, which is preferably present as admixture with isobutyric anhydride and acetic anhydride; 2-methylbutyric-valeric anhydride, which is preferably present as admixture with 2-methylbutyric anhydride and valeric anhydride; propionic-isobutyric anhydride, which is preferably present as admixture with propionic anhydride and isobutyric anhydride; and butyric-valeric anhydride, which is preferably present as admixture with butyric anhydride and valeric anhydride.

More preferred anhydrides are isobutyric anhydride, 2-methylbutyric anhydride, 2-methylhexanoic anhydride, 3-methylhexanoic anhydride, 2-propylheptanoic anhydride, isononanoic anhydride, cyclohexanecarboxylic anhydride, 2-ethylhexanoic anhydride, caprylic anhydride, n-valeric anhydride, isovaleric anhydride, caproic anhydride, and lauric anhydride. Most preferred is isobutyric anhydride.

The anhydride is reacted with a peroxyacid. The peroxyacid has the formula $R^3$—C(=O)—OOH, wherein $R^3$ is selected from linear and branched alkyl, cycloalkyl, aryl, and alkaryl groups with 1 to about 17 carbon atoms, optionally substituted with oxygen- and/or halogen-containing substituents.

Examples of suitable substituents are alkoxy, chlorine, and ester substituents.

The number of carbon atoms is preferably 1 to about 11, more preferably 1 to about 9, and most preferably 1 to about 6.

In a further preferred embodiment, $R^3$ is a linear or branched alkyl group.

Suitable peroxyacids include peracetic acid, propaneperoxoic acid, n-butaneperoxoic acid, isobutaneperoxoic acid, 2,2-dimethylpropaneperoxoic acid, n-pentaneperoxoic acid, 3-methyl butaneperoxoic acid, 2-methyl butaneperoxoic acid, 2-ethyl butaneperoxoic acid, n-hexaneperoxoic acid, octaneperoxoic acid, 4-methylpentaneperoxoic acid, n-heptaneperoxoic acid, n-nonaneperoxoic acid, n-decaneperoxoic acid, neodecaneperoxoic acid, undecaneperoxoic acid, dodecaneperoxoic acid, neoheptaneperoxoic acid, tridecaneperoxoic acid, 2-ethyl hexaneperoxoic acid, tetradecaneperoxoic acid, octadecaneperoxoic acid, phenylethaneperoxoic acid, cyclohexaneperoxoic acid, 3-methylcyclopentaneperoxoic acid, beta-methoxy propaneperoxoic acid, alpha-ethoxy butaneperoxoic acid, perbenzoic acid, o-, m-, and p-methyperlbenzoic acid, 2,4,6-trimethylperbenzoic acid, o-, m-, and p-chloroperbenzoic acid, o-, m-, and p-bromoperbenzoic acid, o-, m-, and p-nitroperbenzoic acid, o-, m- and p-acetoxyperbenzoic acid, o-, m-, and p-aminoperbenzoic acid, and o-, m-, and p-methoxyperbenzoic acid.

Preferred peroxyacids include peracetic acid, propaneperoxoic acid, n-butaneperoxoic acid, isobutaneperoxoic acid, n-pentaneperoxoic acid dimethylpropaneperoxoic acid, 2-methylbutaneperoxoic acid, n-decaneperoxoic acid, dodecaneperoxoic acid and 2-ethyl hexaneperoxoic acid.

More preferred peroxyacids are peracetic acid, propaneperoxoic acid, n-butaneperoxoic acid, isobutaneperoxoic acid and n-pentaneperoxoic acid.

The most preferred peroxyacid is peracetic acid, which means that $R^1=CH_3$. The advantage of peracetic acid is that it is relatively inexpensive and can be produced as a distillate with low $H_2O_2$ and acetic acid content, as described in, e.g., U.S. Pat. No. 3,264,346.

The peroxyacids can be used in pure form or in a solution in water or organic solvent. Suitable organic solvents are alkanes (e.g. isododecane, Spiridane®, and Isopar® mineral oils), chloroalkanes, esters (e.g. ethyl acetate, methyl acetate, dimehylphthalate, ethylene glycol dibenzoate, dibutyl maleate, di-isononyl-1,2-cyclohexanedicarboxylate (DINCH), dioctyl terephthalate, or 2,2,4-trimethylpentanediol diisobutyrate (TXIB)), ethers, amides, and ketones.

In a most preferred embodiment, the peroxyacid is added as a solution in water, most preferably a about 30 to about 50 wt % aqueous solution.

The reaction of step a) is preferably performed at a temperature in the range of from about −10 to about 60° C., more preferably in the range from about 0 to about 40° C., and most preferably in the range from about 5 to about 40° C.

The molar ratio peroxyacid:anhydride is preferably in the range from about 0.8:1 to about 2.2:1, more preferably from about 0.95:1 to about 2.0:1, and most preferably from about 1.0:1 to about 1.4:1.

The reaction does not require the presence of a solvent. However, if the final product (i.e. the diacyl peroxide) requires dilution in a solvent, a solvent can be pre-charged or dosed to the reaction mixture during the reaction. Suitable solvents are alkanes, chloroalkanes, esters, ethers, amides, and ketones. Preferred solvents are (mixtures of) alkanes, such as isododecane, Spirdane®, Isopar® mineral oils; esters like ethyl acetate, methyl acetate, ethylene glycol dibenzoate, dibutyl maleate, di-isononyl-1,2-cyclohexanedicarboxylate (DINCH), or 2,2,4-trimethylpentanediol diisobutyrate (TXIB); and phthalates, such as dimethylphthalate or dioctyl terephthalate.

A base may be present during the reaction. Examples of suitable bases are alkylated amines, oxides, hydroxides, bicarbonates, carbonates, and carboxylates of magnesium, lithium, sodium, potassium, or calcium. The reaction is preferably performed at a pH of at least about 4, more preferably at least about 5.

According to step b), the carboxylic acid is extracted or separated from the mixture obtained in step a) in the form of its carboxylic acid salt or adduct. The formation of said salt or adduct requires the presence of a base. If no base was present during step a) or if the amount of base added during step a) is insufficient to transform the majority of carboxylic acid into the corresponding salt or adduct, a base or an additional amount of base may be added in step b). If the amount of base present in the mixture resulting from step a) is sufficient to transform the majority of carboxylic acid into the corresponding salt or adduct, then no additional amount of base needs to be added in step b).

Suitable bases are alkylated amines, oxides, hydroxides, bicarbonates, carbonates, and carboxylates of magnesium, lithium, sodium, potassium, or calcium. These bases will deprotonate the carboxylic acid, thereby forming a water-soluble salt that ends up in the aqueous phase. The organic phase and the aqueous phase are subsequently separated.

Other suitable bases are solid materials with basic functions that are able to capture the carboxylic acid, thereby forming an adduct. Examples of such solid materials are basic ion exchange resins such as poly(styrene-co-vinylbenzylamine-co-divinylbenzene), N-{2-[bis(2-aminoethyl)amino]ethyl}-aminomethyl-polystyrene, diethylaminomethyl-polystyrene, dimethylamino-methylated copolymers of styrene and divinylbenzene, polymer-bound morpholine, poly(4-vinylpyridine), zeolites or mesoporous silicas containing alkylamine groups like 3-aminopropylsilyl-functionalized SBA-15 silica, polymeric amines, and mixtures of one or more of these materials. The formed adduct can be removed from the reaction mixture by filtration.

Any residual peroxy compounds in the aqueous phase can be removed by washing the aqueous phase with a solvent and/or an anhydride, preferably the anhydride of formula $R^1$—C(=O)—O—C(=O)—$R^2$.

After removal of the carboxylic acid, the organic phase containing the diacyl peroxide may be purified and/or dried. Purification can be performed by washing with water, optionally containing salts, base, or acid, and/or filtration over, e.g., carbon black or diatomaceous earth. Drying can be performed by using a drying salt like $MgSO_4$ or $Na_2SO_4$ or by using an air or vacuum drying step. If the diacyl peroxide is to be emulsified in water, a drying step can be dispensed with.

In step c), the carboxylic acid is liberated by, for instance,
 (i) acidifying the aqueous phase containing the carboxylic acid salt,
 (ii) splitting the adduct (e.g. by heating or acidification) and physically separating (e.g. distilling) the carboxylic acid from the solid material with basic functions, or
 (iii) splitting the salt via electrochemical membrane separation, e.g., bipolar membrane electrodialysis (BPM).

Preferred acids for acidifying and protonating the carboxylic acid are acids with a pKa below about 3, such as $H_2SO_4$, HCl, $NaHSO_4$, $KHSO_4$, and the like. Most preferably $H_2SO_4$ is used. If $H_2SO_4$ is used, it is preferably added as an about 90 to about 96 wt % solution.

Acidification is preferably performed to a pH below about 6, more preferably below about 4.5, and most preferably below about 3. The resulting pH is preferably not lower than about 1.

In addition to acid, also a small amount of a reducing agent, such as sulfite and/or iodide, may be added to the aqueous phase in order to decompose any peroxide residues.

A thermal treatment (e.g. at about 20 to about 80° C.) can be applied in order to decompose any diacyl peroxide residues.

The organic layer containing the carboxylic acid is then separated from any aqueous, salt-containing layer. Separation can be performed by gravity, using conventional separation equipment, such as a liquid/liquid separator, a centrifuge, a (pulsed and or packed) counter current column, (a combination of) mixer settlers, or a continues (plate) separator.

In some embodiments the separation can be facilitated by salting out the organic liquid phase with a concentrated salt solution, e.g. an about 20 to about 30 wt % NaCl, $NaHSO_4$, $KHSO_4$, $Na_2SO_4$, or $K_2SO_4$ solution. The salt reduces the solubility of the carboxylic acid in the aqueous liquid phase. This extraction can be performed in any suitable device, such as a reactor, centrifuge, or mixer-settler.

Especially for lower molecular weight acids, like butyric, isobutyric, pentanoic, and methyl- or ethyl-branched pentanoic acids, a residual amount of the acid will remain dissolved in the aqueous layer. This residual amount can be recovered by adsorption, (azeotropic) distillation, or extraction. Optionally, a salt (e.g. sodium sulfate) can be added to the aqueous layer in order to lower the solubility of the carboxylic acid.

In another embodiment, liberation of the carboxylic acid is achieved by electrochemical membrane separation. Examples of electrochemical membrane separation techniques are membrane electrolysis and bipolar membrane electrodialysis (BPM). BPM is the preferred electrochemical membrane separation method.

Electrochemical membrane separation leads to splitting of the metal carboxylate in carboxylic acid and metal hydroxide (e.g. NaOH or KOH) and separation of both species. It thus leads to (i) a carboxylic acid-containing mixture and (ii) a NaOH or KOH solution, separated by a membrane.

The NaOH or KOH solution can be re-used in the process of the present disclosure, for instance in step a).

Depending on the temperature, the salt concentration, and the solubility of the carboxylic acid in water, the carboxylic acid-containing mixture can be a biphasic mixture of two liquid phases or a homogeneous mixture. If a homogeneous mixture is formed under the electrochemical membrane separation conditions (generally from about 40 to about 50° C.), cooling of the mixture to temperatures below about 30° C. and/or the addition of salt will ensure that a biphasic mixture will be formed. The organic liquid layer of this biphasic carboxylic acid-containing mixture can then be separated from the aqueous layer by gravity or by using equipment like a centrifuge.

The carboxylic acid-containing organic phase is optionally purified to remove volatiles like alcohols, ketones, alkenes and water before it is used in step e). These volatiles can be removed by adsorption, distillation, or drying with salt, molecular sieves, etc. Distillation is the preferred way of purification. The distillation preferably involves two product collection stages, one to collect impurities like alcohols and another to collect the remaining water, optionally as an azeotrope with the carboxylic acid.

According to steps e) and f), the carboxylic acid is subsequently reacted with an acid anhydride or a ketene of the formula $C(R^4)_2$=C=O—each $R^4$ being independently selected from H and $CH_3$—preferably with acetic anhydride, to form an anhydride with the formula $R^1$—C(=O)—O—C(=O)—$R^2$, which is subsequently at least partly recycled to step a) and used again to produce the diacyl peroxide.

The reaction of step e), in particular the reaction with acetic anhydride, is advantageously performed in a reactive distillation column that is fed in the middle sections with the carboxylic acid and the acetic anhydride. The product anhydride is drawn from the bottom of the column and the product acetic acid is collected from the top of the column. An alternative method is to produce the anhydride in a stirred reactor surmounted by a distillation column. This allows the acetic acid to be distilled when formed in order to shift the equilibrium. US 2005/014974 discloses a process to prepare isobutyric anhydride by reacting acetic anhydride with isobutyric acid and containing a step of distilling of the acetic acid as formed. The distillation column is preferably sufficiently efficient to get high purity acetic acid. The efficiency of the column is preferably at least 8 theoretical plates. High purity acetic acid can be sold and/or used for various purposes.

The reaction with the ketene of the formula $C(R^4)_2$=C=O is preferably performed in a counter-current adsorption device, as disclosed in U.S. Pat. No. 2,589,112. The preferred ketene has the formula $CH_2$=C=O.

A catalyst may be used in step e), although it is preferred to perform the reaction in the absence of catalyst. Examples of suitable catalysts are oxides, hydroxides, bicarbonates, carbonates, and carboxylates of magnesium, lithium, sodium, potassium, or calcium.

The molar ratio of carboxylic acid to acetic anhydride is preferably in the range from about 0.5:1 to about 5:1, more preferably from about 1.5:1 to about 2.2:1, most preferably from about 1.8:1 to about 2.2:1. A slight excess of carboxylic acid relative to acetic anhydride might be used.

The reaction is preferably performed at a temperature of from about 70 to about 200° C., preferably from about 100 to about 170° C., most preferably from about 120 to about 160° C. The temperature can be maintained at the desired value by adjusting the pressure in the reactor. This pressure is preferably in the range from about 1 to about 100 kPa, more preferably from about 5 to about 70 kPa.

After completion of the reaction, any excess acetic anhydride that may be present can be distilled off in order to purify the anhydride of formula $R^1$—C(=O)—O—C(=O)—$R^2$. This anhydride can then be used again in step a).

In a preferred embodiment, the carboxylic acid that is used in step e) is obtained from two or three sources. The first source is the carboxylic acid that is liberated in step c). The second source is the carboxylic acid obtained by oxidation of the corresponding aldehyde in accordance with step d), as described below. The third source is an additional amount of carboxylic acid obtained in any other way.

As oxygen source for step d), air is preferably used, although pure oxygen or oxygen-enriched or oxygen-lean air may also be applied. The oxygen source can be added to the reaction mixture by feeding it as a gas to the reactor, preferably using a sparger.

The reaction of step d) is preferably performed at a temperature in the range of from about 0 to about 70° C., more preferably in the range from about 10 to about 60° C., and most preferably in the range from about 20 to about 55° C.

Atmospheric pressure is preferably used; at lower pressure the aldehyde may evaporate, which is undesired.

A catalyst may optionally be used. Very good catalysts which not only accelerate oxidation but also increase the yield of acid are platinum black and ferric salts. Cerium, nickel, lead, copper and cobalt salts are also useful, particularly their carboxylic acid salts.

The catalyst may be added in amounts of from about 0 to about 20 mol % relative to aldehyde, more preferably from about 0 to about 5 mol %, and most preferably from about 0 to about 2 mol %.

Both symmetrical and asymmetrical diacyl peroxides can be produced by the process of the present disclosure. If $R^1$, $R^2$, and $R^3$ in the above formulae are equal, a symmetrical diacyl peroxide will result. Examples of symmetrical diacyl peroxides for which this process is especially suitable are di-propanoyl peroxide, di-2-methylbutyryl peroxide, di-isovaleryl peroxide, di-n-valeryl peroxide, di-n-caproyl peroxide, and di-isobutyryl peroxide.

Asymmetrical diacyl peroxides are, however, the preferred products of this process, more in particular acetyl-acyl peroxides. This is because peracetic acid is the most preferred peroxyacid to be used. Examples of particularly preferred diacyl peroxides for which this process is especially suitable are acetyl-isobutanoyl peroxide, acetyl 3-methylbutanoyl peroxide, acetyl 2-methylbutanoyl peroxide, acetyl lauroyl peroxide acetyl isononanoyl peroxide, acetyl cyclohexylcarboxylic peroxide, acetyl 2-propylheptanoyl peroxide, acetyl p-methylbenzoyl peroxide, and acetyl 2-ethylhexanoyl peroxide.

Other examples of suitable asymmetrical diacyl peroxides are propanoyl 2-methylbutyryl peroxide, butyryl 2-methylbutyryl peroxide, pentanoyl 2-methylbutyryl peroxide, isobutyryl 2-methylbutyryl peroxide, hexanoyl 2-methylbutyryl peroxide, propanoyl isovaleryl peroxide, butyryl isovaleryl peroxide, valeryl isovaleryl peroxide, isobutyryl isovaleryl peroxide, hexanoyl isovaleryl peroxide, propanoyl valeryl peroxide, butyryl valeryl peroxide, isobutyryl valeryl peroxide, hexanoyl valeryl peroxide, propanoyl hexanoyl peroxide, butyryl hexanoyl peroxide, isobutyryl hexanoyl peroxide, propanoyl isobutyryl peroxide, butyryl isobutyryl peroxide, pentanoyl isobutyryl peroxide, hexanoyl isobutyryl peroxide, propanoyl butyryl peroxide, pentanoyl butyryl peroxide, hexanoyl butyryl peroxide, propanoyl cyclohexylcarboxyl peroxide, butyryl cyclohexylcarboxyl peroxide, pentanoyl cyclohexylcarboxyl peroxide, isobutyryl cyclohexylcarboxyl peroxide, hexanoyl cyclohexylcarboxyl peroxide, propanoyl 2-ethylhexanoyl peroxide, isobutyryl 2-ethylhexanoyl peroxide, butyryl 2-ethylhexanoyl peroxide, propanoyl isononanoyl peroxide, isobutyryl isononanoyl peroxide, butyryl isononanoyl peroxide, propanoyl octanoyl peroxide, isobutyryl octanoyl peroxide, valeryl isononanoyl peroxide, and butyryl octanoyl peroxide, of which propanoyl isovaleryl peroxide, propanoyl valeryl peroxide, propanoyl isobutyryl-peroxide, propanoyl isononanoyl peroxide, propanoyl octanoyl peroxide, and valeryl isononanoyl peroxide are preferred.

The process according to the present disclosure and individual steps thereof can be performed batch-wise or continuously. Steps that are preferably performed in continuous mode are reactive distillation to make the anhydride in step e) and isolation and purification of the carboxylic acid in step c).

Also, combinations of batch and continuous operation can be used. Examples of combination are:
- a batch reaction to the diacyl peroxide in step a), followed by a batch separation and continuous purification of carboxylic acid and continuous reactive distillation towards the anhydride in step e),
- a continuous reaction to diacyl peroxide and separation and purification of the carboxylic acid, followed by a batch mode distillation to the anhydride in step e),
- a continuous reaction to peroxyacid, followed by a continuous reaction to diacyl peroxide and separation and purification of the carboxylic acid, followed by a batch mode distillation to the anhydride in step e), or
- a batch reaction to diacyl peroxide and separation of the product, followed by a continuous mode purification of carboxylic acid and continuous reactive distillation to the anhydride in step e).

EXAMPLE

In a 50 ml beaker, equipped with a stirrer and a thermometer and placed in an ice/salt bath, 5.6 g isododecane, 2.0 g 25 wt % NaCl solution, and 5.1 g isobutyric anhydride (0.032 mol) were placed. The mixture was stirred and the temperature was maintained by external cooling at 0° C. while dosing (i) 7.57 g of a 32.4 wt % aqueous peracetic acid solution (0.032 mol) in 20 minutes and (ii) 6.2 g of a 25 wt % NaOH solution (0.039 moles) in 45 minutes.

After 15 minutes post reaction, the layers were allowed to separate by gravity and the water-layer was separated from the organic layer. The organic layer was treated with a mixture of 7 g of a 25 wt % NaCl solution and 4 g of a 6 wt % bicarbonate solution. After separation of the water layer by gravity, the organic layer was analyzed by FT-IR (strong peaks at 1784 $cm^{-1}$, 1049 $cm^{-1}$ and 1814 $cm^{-1}$) to contain 41.1 wt % acetyl isobutyryl peroxide.

The water layer (14.2 grams) was extracted twice with 2.8 g isododecane at 0° C. in order to remove residual peroxides. The extracted aqueous phase was treated with 0.4 g $Na_2SO_3$ in order to decompose remaining peroxyacid.

Subsequently, 1.8 g 96 wt % $H_2SO_4$ was added to lower the pH to 2.5. The layers were allowed to separate by gravity at 40° C. The $Na_2SO_4$-containing water layer, additionally containing 2.5 wt % isobutyric acid—was discarded. The organic phase consisted of 3.3 g wet isobutyric acid.

After azeotropic removal of water in a rotavapor at 200 mbar at 80° C., the isobutyric acid was mixed with isobutyric acid from another source (in this case, from Sigma Aldrich). The isobutyric acid was mixed with acetic anhydride in a molar ratio isobutyric acid:acetic anhydride of 2:1.05 and heated to distill the acetic acid at <400 mbar and 120° C. to obtain isobutyric anhydride as the residue. This anhydride was then recycled to the first step to make acetyl isobutyryl peroxide.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for the production of a diacyl peroxide comprising the following steps:
   a) producing a mixture comprising a diacyl peroxide and a carboxylic acid by reacting an anhydride with the formula $R^1$—C(=O)—O—C(=O)—$R^2$ with a peroxyacid of the formula $R^3$—C(=O)—OOH, wherein $R^1$ and $R^3$ are independently selected from linear and branched alkyl, cycloalkyl, aryl, and arylalkyl groups, each with 1 to 17 carbon atoms, optionally substituted with oxygen- and/or halogen-containing substituents, and $R^2$ is selected from linear and branched alkyl, cycloalkyl, aryl, and arylalkyl groups, each with 2 to 17 carbon atoms, optionally substituted with oxygen- and/or halogen-containing substituents,
- b) extracting or separating the carboxylic acid from the mixture in the form of its carboxylic acid salt or adduct,
- c) liberating the carboxylic acid from the salt or adduct,
- d) optionally producing an additional amount of carboxylic acid by reacting an aldehyde of the formula $R^2$—C(=O)H with oxygen,
- e) reacting the carboxylic acid obtained in step c) and optionally an additional amount of carboxylic acid of the formula $R^2$—C(=O)OH—said additional amount of carboxylic acid being obtained from step d) and/or obtained in another way—with an acid anhydride or a ketene of the formula $C(R^4)_2$=C=O, each $R^4$ being independently selected from H and $CH_3$ to form an anhydride with the formula $R^1$—C(=O)—O—C(=O)—$R^2$, and
- f) recycling at least part of the anhydride formed in step e) to step a).

2. The process according to claim 1 wherein the carboxylic acid is reacted in step e) with acetic anhydride.

3. The process according to claim 1 wherein $R^1$ and $R^2$ are identical.

4. The process according to claim 1 wherein the peroxyacid of the formula $R^3$—C(=O)—OOH is selected from the group of peracetic acid, propaneperoxoic acid, n-butaneperoxoic acid, isobutaneperoxoic acid and n-pentaneperoxoic acid.

5. The process according to claim 1 wherein an additional amount of carboxylic acid is produced in step d) and reacted in step e).

6. The process according to claim 1 wherein the carboxylic acid is extracted in step b) with an aqueous solution of a base to form a carboxylic acid salt and wherein the carboxylic acid is liberated from its salt in step c) by acidification of said extract.

7. The process according to claim 1 wherein the carboxylic acid is extracted in step b) with an aqueous solution of a base to form a carboxylic acid salt and wherein the carboxylic acid is liberated from its salt in step c) by electrochemical membrane separation.

8. The process according to claim 1 further comprising, during step e), acetic acid is produced from the reaction of the acid anhydride and the carboxylic acid obtained in step c), and the acetic acid is removed from the reaction mixture, wherein the acid anhydride is acetic anhydride.

9. The process according to claim 1 wherein step e) is performed in a reactive distillation column.

10. The process according to claim 1 wherein the anhydride with the formula $R^1$—C(=O)—O—C(=O)—$R^2$ is a symmetrical anhydride wherein $R^1$ and $R^2$ are selected from linear and branched alkyl, cycloalkyl, aryl, and arylalkyl groups, each with 2 to 17 carbon atoms, optionally substituted with oxygen- and/or halogen-containing substituents.

11. The process according to claim 1 wherein $R^1$ and $R^2$ are independently selected from linear and branched alkyl groups with 2 to 8 carbon atoms.

12. The process according to claim 10 wherein the anhydride of the formula $R^1$—C(=O)—O—C(=O)—$R^2$ is selected from the group of isobutyric anhydride, 2-methylbutyric anhydride, 3-methylbutyric anhydride, 2-methylhexanoic anhydride, 2-propylheptanoic anhydride, isononanoic anhydride, cyclohexanecarboxylic anhydride, 2-ethylhexanoic anhydride, caprylic anhydride and lauric anhydride.

13. The process according to claim 3 wherein the diacyl peroxide is selected from the group of di-2-methylbutyryl peroxide, di-propionyl peroxide, di-iso-valeryl peroxide, di-n-valeryl peroxide, di-n-caproyl peroxide, and di-isobutyryl peroxide.

14. The process according to claim 4 wherein the diacyl peroxide is selected from the group of acetyl isobutanoyl peroxide, acetyl 3-methylbutanoyl peroxide, acetyl lauroyl peroxide, acetyl isononanoyl peroxide, acetyl 2-methylbutanoyl peroxide, acetyl cyclohexylcarbonyl peroxide, acetyl 2-propylheptanoyl peroxide, acetyl p-methylbenzoyl peroxide, and acetyl 2-ethylhexanoyl peroxide.

15. The process according to claim 4 wherein the diacyl peroxide is selected from the group of propanoyl isovaleryl peroxide, propanoyl valeryl peroxide, propanoyl isobutyryl peroxide, propanoyl isononanoyl peroxide, propanoyl octanoyl peroxide, and valeryl isononanoyl peroxide.

16. The process according to claim 2 wherein $R^1$ and $R^2$ are identical.

17. The process according to claim 2 wherein the peroxyacid of the formula $R^3$—C(=O)—OOH is selected from the group of peracetic acid, propaneperoxoic acid, n-butaneperoxoic acid, isobutaneperoxoic acid and n-pentaneperoxoic acid.

* * * * *